United States Patent
González Ojer et al.

(10) Patent No.: US 9,486,403 B2
(45) Date of Patent: Nov. 8, 2016

(54) GEL COMPOSITIONS

(71) Applicant: LABORATORIOS OJER PHARMA, S.L., Pamplona (ES)

(72) Inventors: Carlos González Ojer, Pamplona (ES); Raquel Maria Da Costa Martins, Barcelona (ES); Josep M. Suñé Negre, Barcelona (ES); Montserrat Miñarro Carmona, Barcelona (ES); Josep Ramon Ticó Grau, Barcelona (ES); Encarna García Montoya, Barcelona (ES); Pilar Pérez Lozano, Barcelona (ES); Manel Roig Carreras, Calafell (ES); Natalia Sánchez Porqueres, Barcelona (ES)

(73) Assignee: LABORATORIOS OJER PHARMA, S.L., Pamplona (ES)

( * ) Notice: Subject to any disclaimer, the term of this patent is extended or adjusted under 35 U.S.C. 154(b) by 0 days.

(21) Appl. No.: 14/652,565

(22) PCT Filed: Dec. 16, 2013

(86) PCT No.: PCT/EP2013/076677
§ 371 (c)(1),
(2) Date: Jun. 16, 2015

(87) PCT Pub. No.: WO2014/095705
PCT Pub. Date: Jun. 26, 2014

(65) Prior Publication Data
US 2015/0343066 A1    Dec. 3, 2015

(30) Foreign Application Priority Data
Dec. 17, 2012  (EP) .................................. 12197473

(51) Int. Cl.
*A61K 31/522* (2006.01)
*A61K 31/575* (2006.01)
*A61K 47/10* (2006.01)
*A61K 47/18* (2006.01)
*A61K 9/06* (2006.01)
*A61K 47/32* (2006.01)
*A61K 9/00* (2006.01)
*A61K 9/70* (2006.01)

(52) U.S. Cl.
CPC ........... *A61K 9/0014* (2013.01); *A61K 9/0048* (2013.01); *A61K 9/06* (2013.01); *A61K 9/7015* (2013.01); *A61K 31/522* (2013.01); *A61K 31/575* (2013.01); *A61K 47/10* (2013.01); *A61K 47/18* (2013.01); *A61K 47/32* (2013.01)

(58) Field of Classification Search
None
See application file for complete search history.

(56) References Cited

FOREIGN PATENT DOCUMENTS

| EP | 1413292 A1 | 4/2004 |
|----|-----------|--------|
| WO | WO2005074883 A1 | 8/2005 |

OTHER PUBLICATIONS

Jones D. S. et al.: "Physicochemical characterization and preliminary in vivo efficacy of bioadhesive, semisolid formulations containing flurbiprofen for the treatment of gingivitis", Journal of pharmaceutical Sciences, American Pharmaceutical Association, Washington, US, vol. 88, No. 6, Jun. 1, 1999 (Jun. 1, 1999), pp. 592-598, XP000825428, ISSN: 0022-3549, DOI: 10.1021/JS9803095.

International Search Report and Written Opinion for PCT/EP2013/076677, European Patent Office, mailed Feb. 6, 2014, pp. 1-13, Rijswijk, NL.

*Primary Examiner* — Samantha Shterengarts
(74) *Attorney, Agent, or Firm* — Peter B. Scull; Hamilton, DeSanctis & Cha, LLP

(57) ABSTRACT

The present invention provides a gel combination comprising: polycarbophil in an amount comprised from 1 to 5% by weight; polyvinylpirrolidone in an amount comprised from 4 to 8% by weight; glycerine in an amount comprised from 1 to 10% by weight; and propyleneglycolin an amount comprised from 20 to 40% by weight; wherein: the weight ratio between polyvinylpirrolidone:polycarbophil is comprised between 1:1 and 4:1, the weight ratio between glycerine:polycarbophil is comprised from 0.5:1 to 2:1, and the weight ratio propyleneglycol:polycarbophil is comprised from 8:1 to 20:1. The invention also provides transparent compositions comprising such gel combinations as well as processes for their preparation and the use thereof as a medicament. Due to the specific excipients, % by weight, and weight ratios forming the combination, the resulting compositions show a high bioadhesivity and bioavailability of the active ingredient, without toxic adverse effects.

18 Claims, 1 Drawing Sheet

GEL COMPOSITIONS

The present invention relates to a combination of polycarbophil, polyvinylpirrolidone, glycerine, and propyleneglycol which, due to the specific weight percentages and ratios, is a gel-forming agent as well as a film-forming agent. The present invention further relates to pharmaceutical and veterinary compositions, as well as to medical devices comprising the combination of the invention.

BACKGROUND ART

Topical administration of active ingredients advantageously allows the maximum concentration of the ingredient directly near the biophase and contemporaneously avoids that its dispersion into tissues may cause unnecessary risks of toxicity or intolerance.

Residence time of the composition at the site of application is critically affected by the consistency of the composition. Therefore, in the particular case of a pharmaceutical composition, a non-optimized vehicle can negatively affect the therapeutic efficacy of such composition.

In the case of cutaneous administration, a high viscosity of the composition requires a stronger spreading, causing burning or pain if the tissues are irritated or damaged; whereas a non-viscous composition can be fastly eliminated from the site of application.

In the particular case of topical pharmaceutical compositions, the sustained release of the active ingredient is frequently addressed. In this regard, the sustained release of an active ingredient involves polymers that typically release the drug at a controlled rate due to diffusion out of the polymer or by dilution of the polymer over time. Topical administration of drugs changes the rate at which drugs enter the tissue and the pharmacokinetics of the drug, thus the correctly designed materials can optimize the therapeutic effect by controlling the drug release rate.

Thus, there remains a long-felt and unmet need for a material which allows the appropriate deliver of the active ingredient.

In addition to the above, the skilled person further faces with other technical drawbacks when formulating a topical pharmaceutical composition, due to the nature of the active ingredient included therein. Some of the active ingredients known in the state of the art have a low solubility in water or are almost totally insoluble in hydrophobic solvent systems.

It is accordingly difficult to produce a topical formulation containing a sufficient dissolved concentration of active ingredient for it to exert its full effect and also to optimize the flux of the compound into the skin.

In addition to ease of release, it is also important that any formulation of a pharmaceutically active compound should be stable for long periods of time, should not lose its potency, should not discolor or form insoluble substances or complexes, and also should not be unduly irritating to the skin or mucosa.

In spite of the efforts made, there is still the need of providing topical compositions with appropriate bioadhesion, stability, and improved bioavailability of the active ingredients included therein.

SUMMARY OF THE INVENTION

The present inventors, in an attempt for developing a gel composition with appropriate bioadhesive properties, have found a combination which solves the above-mentioned problems by selecting specific excipients, in specific amounts, and weight ratios.

Surprisingly, it has been found that a combination comprising polycarbophyl, polyvinylpirrolidone, glycerine, propyleneglycol, and trometamol or a salt thereof, at specific weight percentages and ratios, is able of forming a bioadhesive gel, without the need of incorporating any gel-forming agent.

Thus, in a first aspect the present invention provides a combination comprising the following ingredients:
 polycarbophil in an amount comprised from 1 to 5% by weight,
 polyvinylpirrolidone in an amount comprised from 4 to 8% by weight,
 glycerine in an amount comprised from 1 to 10% by weight, and
 propyleneglycol in an amount comprised from 20 to 40% by weight, wherein:
 the weight ratio polyvinylpirrolidone:polycarbophil is comprised between 1:1 and 4:1,
 the weight ratio glycerine:polycarbophil is comprised from 1:1 to 2:1, and
 the weight ratio propyleneglycol:polycarbophil is comprised from 8:1 to 20:1.

It has been found that the combination of the present invention is able to form a film, when it is deposited on a body tissue.

It is remarkable that none of the excipients forming the combination of the first aspect of the invention is known in the state of the art as gel-forming agent. In fact, polycarbophil is known as bioadhesive agent; polyvinylpirrolidone is known as disintegrant, suspending agent, viscosity-increasing agent, and tablet binder; glycerine is known as humectant agent; and propyleneglycol is known as emulsifying agent, suspending agent, and viscosity-increasing agent.

Until now, it was well-established that any gel composition needed the incorporation of at least one of the gel-forming agents known in the state of the art in order to get such texture. One of the most widely used gel-forming agents is carbopol. It is well-known that the inclusion of a gel-forming agent, such as carbopol, apart of providing such gel texture, increases the viscosity of the resulting composition. As it is well-known for the skilled person in the art, an increase in the viscosity of the composition can negatively affect the diffusion of the agent (which has to exert the intended effect) through the matrix and/or the application of the composition in a specific zone, both of which affecting negatively to the bioavailability of the active ingredient and hence, to the efficacy of the composition.

Surprisingly, a combination such as the one referred in the first aspect of the invention, allows the formation of a gel without the need of including gel-forming agents, such as carbopol. The combination of the invention can be easily applied and, in addition, shows the appropriate viscosity to not adversely affect the bioavailability of the agent included therein. In the latter, as it is illustrated below, one of the most remarkable advantageous features of the combination of the invention is that there is a high bioavailability of the active ingredient included therein, with the subsequent advantages of high efficacy, reduced dose and/or reduced number of applications of the product. Such a high bioavailability characterizing the compositions comprising the combination of the invention is at least due to the appropriate viscosity of the gel matrix combination of the first aspect of the invention.

In addition to the above, the gel formed by the combination of the first aspect of the invention shows bioadhesive properties. As it is shown below, when a composition including the combination of the first aspect of the invention and an active ingredient is applied on a specific zone, it is observed that a high concentration of the active ingredient is in the skin, and that such ingredient diffuses from the gel matrix to the skin, to penetrate it and exert its therapeutic application, without getting the systemic circulation. In order to get such a behavior, the combination of the invention adheres to the body tissue where it is applied, forming a thin film (which is the responsible of the high bioadhesivity observed with the combination of the invention). Due to this strong bioadhesion and the physico-chemical environment properties of the gel matrix (determined by the excipients, percentages, and ratios forming the combination of the invention), the active ingredient diffuses from the gel matrix and penetrates the skin.

A further advantage of the combination of the invention is that when it is applied on epithelial cells, namely skin and mucous membranes (mucosa), no irritation or corrosion is observed (as confirmed with the cutaneous irritation/corrosion tests included below).

In view of the above mentioned advantages of bioadhesivity, bioavailability, and non-toxicity, the combination of the first aspect of the invention becomes a good vehicle for the formulation of pharmaceutical or veterinary compositions.

Thus, in a second aspect, the present invention provides a pharmaceutical or veterinary composition comprising the combination as defined above, together with: (a) a therapeutically effective amount of an active ingredient or a pharmaceutically or veterinary acceptable salt thereof; and (b) other appropriate pharmaceutically or veterinary acceptable excipients and/or carriers.

Many of the commercial gel pharmaceutical or veterinary compositions are characterized by the fact that the active ingredient (which has the intended effect) is precipitated in the matrix. This precipitation, which can be due to a lack of stability in the gel matrix, adversely affects to the bioavailability of the active ingredient.

Surprisingly, the pharmaceutical or veterinary composition of the second aspect, comprising the combination of the invention, is transparent, not being detected any precipitate in the gel matrix. Without being bound to the theory it is believed that the combination of the invention provides a gel matrix with the appropriate physico-chemical environment allowing the stabilization of the active ingredient added, in such a way that no precipitation occurs. Therefore, the combination with such excipients in the specified ratios and percentages of the first aspect of the invention improves the bioavailability of the hydrophilic active ingredient included therein. In this regard, it has also been found that trometamol in the specified weight percentage and ratio, helps in dissolving the active ingredient in the matrix.

The pharmaceutical or veterinary composition of the invention, due to the better bioavailability of the hydrophilic active ingredient, has an improved efficacy. Thus, the dose of the composition required to obtain the desired therapeutic effect is lower and/or the number of applications needed to obtain the desired effect can be reduced.

In the state of the art there are many processes for preparing gel pharmaceutical or veterinary compositions. As the skilled man in the art knows, when preparing such formulations, one of the most critical issues is to obtain the composition without grumes. Many of the processes currently known provide gel compositions with grumes (which can be visually observed). Such compositions with grumes are not acceptable from the pharmaceutical point of view and, therefore, the manufacturers have to spend time and money in further steps/technology for trying to dissolve them.

The inventors of the present invention have developed a process for the appropriate preparation of pharmaceutical or veterinary compositions as defined in the second aspect of the invention.

Thus, in a third aspect the present invention provides a process for preparing the pharmaceutical or veterinary composition as defined above, the process comprising the following steps: (a) mixing the active ingredient or pharmaceutically or veterinary salt thereof with propyleneglycol under agitation; (b) adding the polyvinylpirrolidone; (c) adding the glycerine; (d) adding the polycarbophil; and (e) adding the other appropriate pharmaceutically or veterinary acceptable excipients and/or carriers.

With such a process, the problems of grumes, time consumption, and inversion of high amounts of money in getting such a non-grumes compositions are overcome.

The inventors have found that two aspects of the process are critical for achieving such a composition without grumes: (1) the active ingredient is added prior to the gellification of the combination (which takes place once all four excipients are present, that is after performing step (d)); and (2) the incorporation of the active ingredient to propyleneglycol has to be performed under agitation.

Due to the absence of precipitates and grumes, the pharmaceutical or veterinary compositions of the present invention are transparent.

Furthermore, the compositions of the invention are also stable.

The pharmaceutical or veterinary composition can be administered in several forms, as it is explained in detail below. Among them, the composition of the second aspect of the invention can be manufactured in the form of a kit.

Thus, in a fourth aspect the present invention provides a kit comprising the combination as defined in the first aspect of the invention or the composition as defined in the second aspect of the invention, and a support.

As it has been deeply discussed above, the combination of the present invention acts as gel-forming agent due to the specific selection of excipients, weight percentages, and ratios.

Therefore, in a fifth aspect, the present invention provides the use of the combination of the first aspect of the invention as gel-forming agent.

In addition, as it has been explained above, when the combination of the invention is applied on a body tissue (such as skin, mucosa, among others), it forms, immediately after the contact, a film. Without being bound to the theory, it is believed that when the combination of the invention is applied on the body tissue.

Thus, in a sixth aspect, the present invention provides the use of the combination as defined above, as a film-forming agent by depositing the combination on a body tissue, thereby absorbing the moisture from the tissue, and forming a film over the surface of the body tissue.

Finally, in a seventh aspect, the present invention provides a pharmaceutical or veterinary composition as defined above, for use as a medicament.

DETAILED DESCRIPTION OF THE INVENTION

Figure 1:
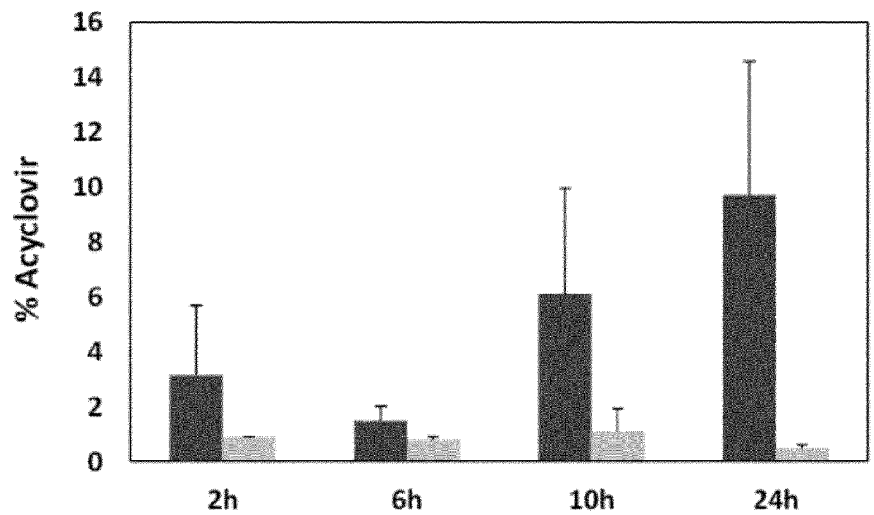
FIG. 1 shows the total amount of acyclovir (%) in samples of human skin, after 5 applications of Formulation 1 (black bar) or the reference composition (grey bar) at times 2, 6, 10 h, and 24 h. It is observed an "accumulative effect" when it is applied the composition of the invention, being the concentration of acyclovir 5 or 21 times higher when compared with the concentration of acyclovir available when the reference composition is applied. Y-axis: mg acyclovir; X-axis: time (expressed in hours) at which the samples are taken.

As it has been stated above, the present invention provides a combination of polycarbophil, polyvinylpirrolidone, glycerine, and propyleneglycol in specific weight amounts and ratios.

The term "percentage (%) by weight" refers to the percentage of each ingredient of the combination in relation to the total weight.

The term "weight ratio" refers to the relation of weights of polycarbophil: polyvinylpirrolidone, and of glycerine: propyleneglycol.

In the present invention, the term "polycarbophil" has to be understood as a high molecular weight acrylic acid polymer crosslinked with divinyl glycol of formula (I).

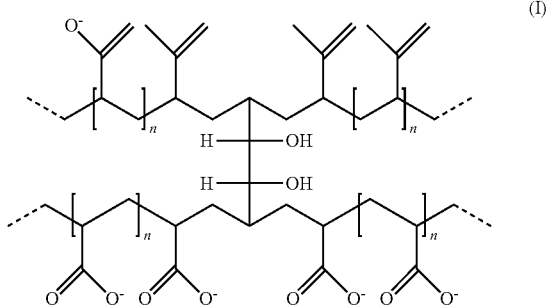
(I)

It has been used extensively to enhance the delivery of active ingredients to various mucous membranes.

In the present invention, the term "polyvinylpirrolidone", and molecular formula (C6H9NO)n, has to be understood as a water-soluble polymer made from the monomer N-vinylpyrrolidone:

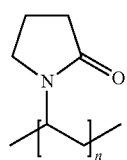
(II)

and has the CAS number 9003-39-8. The mechanism for terminating the polymerization reaction makes it possible to produce soluble polyvinylpyrrolidone of almost any molecular weight. Different chain lengths yield in different viscosities. Traditionally, the degree of polymerization is characterized by the K-value, which is essentially a function of the viscosity in aqueous solution (illustrative non-limitative examples: K-15, K-25, K-30, K-60 and PVP K-90).

In one embodiment, the polycarbophil is in an amount of 3% by weight.

In another embodiment, the polyvinylpirrolidone is in an amount of 6% by weight.

In still another embodiment, the glycerine is in an amount of 2% by weight.

In still yet another embodiment, the propyleneglycol is in an amount of 30% by weight.

In the present invention the term "gel" has to be understood as a semisolid form, consisting of a liquid gelled (such as water or alcohol) by the aid of the combination of the invention. In these semisolid systems the liquid phase is confined within a three dimensional matrix with certain reticulation degree.

In the present invention, the term "hydrogel" has to be understood as a three-dimensional, hydrophilic, polymeric networks capable of imbibing large amounts of water or biological fluids. The networks are composed of homopolymers or copolymers, and are insoluble due to the presence of chemical crosslinks (tie-points, junctions), or physical crosslinks, such as entanglements or crystallites. The latter provide the network structure and physical integrity. These hydrogels exhibit a thermodynamic compatibility with water which allows them to swell in aqueous media.

In one embodiment of the first aspect of the invention, the ratio policarbophil:polyvinylpirrolidone is 0.5:1.

In another embodiment of the first aspect of the invention, the weight ratio polyvinylpirrolidone:polycarbophil is 2:1.

In another embodiment of the first aspect of the invention, the weight ratio between glycerine:polycarbophil is comprised from 0.5:1 to 1:1.

In another embodiment of the first aspect of the invention, the weight ratio propyleneglycol:polycarbophil is 10:1.

In one embodiment of the first aspect of the invention, the combination includes a pH-regulating agent.

Illustrative non-limitative examples of pH-regulating agents include, among others, acetic acid, lactic acid, citric acid, ethanolamine, formic acid, oxalic acid, potassium hydroxide, sodium hydroxide, triethanolamine, citric acid, monosodium or monopotassium citrate, disodium or dipotassium citrate, trisodium or tripotassium citrate, phosphoric acid, monosodium or monopotassium phosphate, disodium or dipotassium phosphate, trisodium or tripotassium phosphate, glycine, trometamol, or their mixtures. Preferably, the pH-regulating agent is trometamol. It has been found that the inclusion of trometamol in the combination of the invention improves the stability of the resulting gel and helps in dissolving the active ingredient in the matrix.

In one embodiment of the first aspect of the invention, the combination comprises trometamol in a % by weight comprised from 1 to 5%, and in a weight ratio trometamol: polycarbophil 1:1.

Preferably, the combination of the first aspect of the invention is one comprising:
polycarbophil: 3% by weight
polyvinylpirrolidone: 6% by weight,
glycerine: 2% by weight,
propyleneglycol: 30% by weight, and
trometamol: 3% by weight.

As mentioned above, in a further aspect the present invention provides a pharmaceutical or veterinary composition comprising the combination of the first aspect of the invention, together with: (a) a therapeutically effective amount of an active ingredient or a pharmaceutically acceptable salt thereof; and (b) appropriate pharmaceutically or veterinary acceptable excipients and/or carriers.

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The active ingredient can be selected from hydrophilic or hydrophobic active ingredients, which can be optionally encapsulated. Illustrative non-limitative examples of active ingredients that can be included in the composition of the invention are: chemotherapeutics including antivirals (such as acyclovir, penciclovir, valaciclovir, idoxuridine, tromantadine, imiquimod, and metronidazole; antibiotics (such as fusidic acid, mupirocin, gentamicin, neomycin, retapamulin, clindamycin, erythromycin, and chlortetracycline); antifungals such as imidazole and triazole derivatives (including bifonazole, chlotrimazole, eberconazole, econazole, fenticonazole, flutrimazole, ketoconazole, miconazole, oxiconazole, sertaconazole, thioconazole); nistatin, Naftifine, terbinafine, tolnaftate, and ciclopirox; healing agents, such as *Arnica montana, Centella asiatica*, and becaplermin; topical anti-histaminic agents such as diphenydramine, dimetindene, and promethazine; local anesthetics, such as lidocaine, benzocaine, and tetracaine; anti-psoriatic agents, such as etanercept, adalimumab, ustekinumab, dithranol, calcipotriol, calcitriol, tacalcitol, and tazarotene; anti-inflammatory agents such as those of stereoid nature (including dexamethasone, prednisolone, triamcinolone, fluorometholone, betamethasone, budesonide, hydrocortisone, clobetasone, beclometasone, desoximetasone, methylprednisolone), and non-stereoid agents (AINE) (including dicoflenac, aceclofenac, benzydamine, dexketoprofen, etofenamate, fepradinol, ibuprofen, indomethacin, ketoprofen, piroxicam); retinoid agents (such as tretinoin, isotretinoin, and adapalene); antiseptic and desinfectant agents (such as chlorhexidine, boric acid, triclosan); tacrolimus; hydroquinone; minoxidil; Finasteride.

In one embodiment of the second aspect of the invention, the composition is in the form of a hydrogel and the active ingredient is: i) a hydrophilic active ingredient or a salt thereof, which is optionally encapsulated, or, alternatively, (ii) an encapsulated hydrophobic active ingredient.

In the present invention, the term "hydrophilic active ingredient" is to be understood as a drug that charge-polarized and capable of hydrogen bonding, enabling it to dissolve more readily in water than in oil or other hydrophobic solvents. It is also known as "polar drug" and, both terms can be used interchangeably.

In the present invention, the term "hydrophobic active ingredient" is to be understood as a drug which tends to be non-polar and, thus, prefer other neutral molecules and non-polar solvents rather than water. Hydrophobic molecules in water often cluster together, forming micelles.

As it is well-known for the skilled person in the art, a parameter useful to determine whether an active ingredient is hydrophilic or hydrophobic is determining its partition coefficient (P). The partition (P) coefficient is the ratio of concentrations of a particular compound in a mixture of two immiscible phases at equilibrium. Normally one of the solvents chosen is water while the second is hydrophobic such as octanol. Hydrophobic active ingredients have high octanol/water partition coefficients, and hydrophilic active ingredients have low octanol/water partition coefficients. The log P value is also known as a measure of lipophilicity/hydrophilicity. The logarithm of the ratio of the concentrations of the un-ionized solute in the solvents, at a specific pH, is called log P: The log P value is also known as a measure of lipophilicity:

$$\log P_{oct/wat} = \log\left(\frac{[\text{solute}]_{octanol}}{[\text{solute}]_{water}^{un-ionized}}\right)$$

wherein the "solute" is the active ingredient.

In the present invention, the expression "encapsulated" is to be understood as being enclosed in micro- or nanodelivery systems, such as a microparticle or nanoparticle.

The term "microparticle" is to be understood as relatively solid spherical particles, with diameter between 1 and 1000 micrometers, that form a continuous network or matrix system composed by one or more polymeric substances, in which the active ingredient is dispersed. According to their structure, microparticles can be classified in microcapsules and microspheres. Thus, microcapsules are vesicular systems in which the active ingredient is confined to a cavity and is surrounded by a polymeric membrane; and microspheres are matricial systems in which the active ingredient is dispersed.

The term "nanoparticle" as used herein, refers to a particle with at least two dimensions at the nanoscale, particularly with all three dimensions at the nanoscale, where the nanoscale is the range about 1 nm to about 1000 nm.

In the present invention, the term "a pharmaceutically or veterinary acceptable salt" is to be understood as encompassing any salt formed from pharmaceutically or veterinary acceptable non-toxic acids including inorganic or organic acids. There is no limitation regarding the salts, except that if used for therapeutic purposes, they must be pharmaceutically acceptable. Such acids include for instance acetic, benzenesulfonic, benzoic, camphorsulfonic, citric, ethansulfonic, fumaric, gluconic, glutamic, hydrobromic, hydrochloric, lactic, maleic, malic, mandelic, methanesulfonic, phosphoric, sorbic, succinic, sulfuric, tartaric, p-toluensulfonic acid, and the like.

The preparation of pharmaceutically or veterinary acceptable salts of the hydrophilic active ingredients can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically acceptable base or acid in water or in an organic solvent or in a mixture of them.

In the present invention, the term "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. Likewise, the term "veterinary acceptable" means suitable for use in contact with a non-human animal.

As it is shown below, in the section Examples, when the pharmaceutical composition of the invention is applied and the skin samples are analyzed, at different times, it is observed a great increase in the concentration of the active ingredient in the skin when compared with the reference.

In one embodiment, the pharmaceutical or veterinary composition of the second aspect of the invention shows a sustained release profile.

In the present invention, the expression "sustained release profile" has to be understood as a release of the active ingredient at a predetermined rate in order to maintain a constant drug concentration for a specific period of time with minimum side effects.

The pharmaceutical or veterinary composition of the present invention can be applied in any suitable form, such as topically, intradermally or transdermally. Preferably, the composition is applied topically.

In one embodiment, the pharmaceutical or veterinary composition shows a sustained release and is applied topically.

In another embodiment, the pharmaceutical or veterinary composition is in the form of a bioadhesive film.

Several procedures are well-known in the state of the art for preparing a bioadhesive film.

For the topical administration, appropriate pharmaceutical excipients or carriers include, but do not limit to, hydrating agents, emollients, emulsifiers, humectants, pH-regulating agents, antioxidants, preservative agents, vehicles, or mixtures thereof. The excipients or carriers used have affinity for the skin, are well tolerated, stable, and are used in an amount adequate to provide the desired consistency, and ease application.

When the pharmaceutical composition of the present invention is topical, it can be formulated in several forms that include, but are not limited to, solutions, suspensions, hydrogels, emulgels, lyogels, lotions, gels, ointments, pastes, and creams, among others. These topical pharmaceutical compositions can be prepared according to methods well known in the state of the art. The appropriate pharmaceutical excipients and/or carriers, and their amounts, can readily be determined by those skilled in the art according to the type of formulation being prepared.

Examples of appropriate topical hydrating agents include, among others, collagen, collagen amino acids, dimethiconol, glycine, hyaluronic acid, dimethylsilanol hyaluronate, magnesium stearate, maltitol, maltose, pyrrolidone carboxylic acid (PCA), manganese PCA, sodium PCA, mannitol, trehalose, trilactin, glucose, glutamic acid, erythritol, aluminium stearoyl glutamate, copper acetylmethionate, or ditridecyl dimmer dilinoleate.

Examples of appropriate emulsifier include, among others, glyceryl trioleate, glyceryl oleate, acetylated sucrose distearate, sorbitan trioleate, polyoxyethylene monostearate, glycerol monooleate, sucrose distearate, polyethylene glycol monostearate, octyl phenoxypoly (ethyleneoxy) ethanol, deacylerin penta-isostearate, sorbitan sesquioleate, hydroxylated lanolin, lecithin, lanolin, triglyceryl diisostearate, polyoxyethylene oleyl ether, calcium stearoyl-2-lactylate, sodium lauroyl lactylate, sodium stearoyl lactylate, ceteary glucoside, methyl glucoside sesquistearate, sorbitan monopalmitate, methoxy polyethylene glycol-22/dodecyl glycol copolymer, polyethylene glycol-45/dodecyl glycol copolymer, polyethylene glycol 400 distearate and glyceryl stearate, candelilla/jojoba/rice bran polyglyceryl-3 esters, cetyl phosphate, potassium cetyl phosphate, or their mixtures.

Examples of appropriate cosolvents to assist in dispersing the drug include, among others, oleyl acid, phospholipids, benzyl alcohol, benzyl benzoate, $C_{12}$-$C_{15}$ fatty acid benzoates, and transcutol.

Examples of appropriate chelating agents to assist in the drug dispersion or solubilization are cyclodextrin and polyphosphates.

Examples of appropriate surfactant agents include, among others, non-ionic, ionic (either anionic or cationic) or zwitterionic (or amphoteric wherein the head of the surfactant contains two oppositely charged groups) surfactants. Examples of anionic surfactants are, for instance, those based on sulfate, sulfonate or carboxylate anions such as perfluorooctanoate (PFOA or PFO), alkyl benzene sulfonate, soaps, fatty acid salts, or alkyl sulfate salts such as perfluorooctanesulfonate (PFOS), sodium dodecyl sulfate (SDS), ammonium lauryl sulfate, or sodium lauryl ether sulfate (SLES). Examples of cationic surfactants are, for instance, those based on quaternary ammonium cations such as or alkyltrimethylammonium including cetyl trimethylammonium bromide (CTAB) a.k.a., or hexadecyl trimethyl ammonium bromide, cetylpyridinium chloride (CPC), polyethoxylated tallow amine (POEA), benzalkonium chloride (BAC), or benzethonium chloride (BZT). Examples of zwitterionic surfactants include, but are not limited to dodecyl betaine, cocamidopropyl betaine, or coco ampho glycinate. Examples of non-ionic surfactants include, but are not limited to, alkyl poly(ethylene oxide), alkylphenol poly (ethylene oxide), copolymers of poly(ethylene oxide), poly (propylene oxide) (commercially called Poloxamers or Poloxamines), alkyl polyglucosides including octyl glucoside and decyl maltoside, fatty alcohols including cetyl alcohol and oleyl alcohol, cocamide MEA, cocamide DEA, or polysorbates including tween 20, tween 80, or dodecyl dimethylamine oxide.

Examples of appropriate topical humectants include, among others, glycerine, diglycerine, ethylhexylglycerine, glucose, honey, lactic acid, polyethylene glycol, propylene glycol, sorbitol, sucrose, polydextrose, sodium hyaluronate, sodium lactate, tagatose, or threalose.

Examples of appropriate topical pH-regulating agents include, among others, acetic acid, lactic acid, citric acid, ethanolamine, formic acid, oxalic acid, potassium hydroxide, sodium hydroxide, triethanolamine, citric acid, monosodium or monopotassium citrate, disodium or dipotassium citrate, trisodium or tripotassium citrate, phosphoric acid, monosodium or monopotassium phosphate, disodium or dipotassium phosphate, trisodium or tripotassium phosphate, glycine, or their mixtures.

Examples of appropriate antioxidants include, among others, free radical scavengers or reducing agents such as, acetyl cysteine, ascorbic acid, ascorbyl palmitate, butylated hydroxytoluene, green tea extract, caffeic acid, cysteine, tocopherol, ubiquinone, propyl gallate, butylhydroxyanisol, butylated hydroxytoluene (BHT), and their mixtures.

Examples of appropriate preservative agents include, among others, benzoic acid, butylparaben, ethylparaben, diazohidinyl urea, imidurea, propylparaben, methylparaben, sorbic acid, potassium sorbate, sodium benzoate, phenoxyethanol, triclosan, or their mixtures.

The compositions mentioned above also include a vehicle. Examples of vehicles include, but are not limited to, water, butylene glycol, ethanol, isopropanol, or silicones. Preferably, the vehicle is water.

Additionally, the compositions of the present invention may contain other ingredients, such as fragrances, colorants, and other components known in the state of the art for use in topical formulations.

The pharmaceutical or veterinary composition can be applied to intact or lesioned skin.

Skin lesions can be classified in primary and secondary lesions. Primary skin lesions are variations in color or texture that may be present at birth (such as birthmarks) or that may be acquired during a person's lifetime, such as those associated with infectious diseases (e.g. psoriasis), allergic reactions (e.g. hives or contact dermatitis), or environmental agents (e.g. sunburn, pressure, or temperature extremes). Secondary skin lesions are those changes in the skin that result from primary skin lesions, either as a natural progression or as a result of a person manipulating (e.g. scratching or picking at) a primary lesion. Major types of secondary skin lesions are ulcers, scales, crusts, erosions, excoriation, scars, lichenification, and atrophies, among others.

The present invention provides, in the third aspect of the invention, a process for preparing a pharmaceutical or veterinary composition comprising the combination of the first aspect of the invention. As it has been stated above, such a composition has no grumes.

In one embodiment of the process of the third aspect, the polycarbophil has been previously meshed.

In another embodiment of the process of the third aspect of the invention, the active ingredient, or pharmaceutically or veterinary acceptable salt thereof, is previously dissolved in an alcoholic solvent.

The term "alcoholic solvent" is to be understood as a C1-C10 alcoholic solvent. Illustrative non-limitative examples of alcoholic solvents are methanol, ethanol, propanol, isopropanol, butanol, isobutanol, among others.

The present invention also provides a kit comprising the combination or composition as defined above, and support.

The support can be coated with the combination of the present invention provided that the bioadhesive properties detailed above are maintained. Preferably, the carrier material is coated, and more preferably, it is coated by one side. In the case of coating, no drying step is performed (in such a case the combination or composition of the invention would lose its advantageous properties).

In the present invention, the term "support" has to be understood as any conventional carrier material known for use in dressings. It is preferable that the carrier material is made from inelastic fibers. The carrier material is generally either knitted, extruded, woven, or non-woven. It is optionally in the form of a foam or film. The fibres are made from cotton, rayon, polyester, polyamide, polypropylene, polyamide or wool or a mixture thereof.

Processes for the preparation of such a medical devices are well-known for those skilled in the art.

In addition, the kit can include instructions for its use in any of the applications mentioned above.

In a sixth aspect, the present invention provides the combination of the invention as a film-forming agent by depositing the combination on a body tissue, thereby absorbing the moisture from the tissue, and forming a film over the surface of the body tissue.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1

Formulation with the Combination of the Invention and Acyclovir (Formulation 1)

TABLE 1

| Ingredient | amount |
|---|---|
| Acyclovir | 5 g |
| Polycarbophil (Noveon AA-1) | 3 g |
| PVP 30 | 6 g |
| Menthol crystal | 0.10 g |
| Trometamol | 3 g |
| Glycerine | 2 g |
| Propyleneglycol | 30 g |
| Deionized water | 50.90 g |

All the components were weighted in commercial precision balances. Then, the menthol crystal was sprayed in a mortar and, subsequently, it was dissolved, under agitation, in propyleneglycol. The solution was incorporated in a precipitate vessel and, under agitation, acyclovir was incorporated.

On the other hand, trometamol were dissolved in deionized water. Then, povidone was incorporated and dissolved, under agitation, in the trometamol solution. The resulting solution was incorporated in the acyclovir solution previously obtained and, using an emulsifier Bi-agi®, the glycerine was incorporated. Once incorporated, Noveon AA-1 was meshed (mesh size: 0.5 mm) and slowly incorporated to the emulsion using the commercial emulsifier Bi-agi®, thus obtaining the Formulation 1.

Example 2

Formulation with the Combination of the Invention and Fusidic Acid (Formulation 2)

TABLE 2

| Ingredient | amount |
|---|---|
| Fusidic acid | 2 g |
| Polycarbophil (Noveon AA) | 3.2 g |
| Povidone (PVK 29/32) | 5.00 g |
| Tymol | 0.10 g |
| Trometamol | 2.00 g |
| Glycerine | 10.00 g |
| Propyleneglycol | 20.00 g |
| Deionized water | 57.70 g |

The same procedure than the one followed in Example 1 for obtaining Formulation 1 was followed, provided that it was used tymol instead of menthol crystal.

Example 3

Dermal Delivery and Percutaneous Absorption Analysis of Formulation 1

A) Materials and Methods

A.1. Skin membranes from female human abdominal origin from cosmetic surgery were used. Split skin (approx. 500 μm) was prepared with a derrnatome and comprises the stratum corneum, the epidermis, and part of the dermis. Skin pieces were produced for the use in the diffusion cell (10 mm diameter of exposure area) with a punch. The skin pieces were frozen between microscopic slides at −15° C. Thickness of the prepared split skin was measured between the two microscopic slide mounts.

Since membrane preparation could result in damage to the skin, the integrity of the skin membrane was checked before fitting it into the diffusion cell.

A.2. Phosphate buffered saline (PBS) was used as receptor fluid. In order to achieve an air bubble free equilibration of the diffusion test system and the diffusion cells, the receptor fluid was degassed prior to use.

A.3. The diffusion cell was designed with a Poly tetra fluoro ethene (PTFE)-donator and -acceptor part of the flow through diffusion cell for horizontal exposure of the skin surface. Skin exposure area was about 80 mm². The diffusion cells were set in a microprocessor controlled with a thermostatization block. A multi-channel peristaltic pump was connected with the receptor part of the diffusion cell and a programmable fraction collector was responsible for collecting the samples.

The frozen skin was rinsed with the acceptor fluid (PBS) and placed on the acceptor compartment. The diffusion cell was closed with the receptor compartment and equilibrated with degassed receptor fluid (PBS) in horizontal position in the thermoblock. The diffusion cells were adjusted to a temperature of about 32° C.

Finally, the skin assembled in the diffusion cell was checked for barrier integrity using tritiated water. Briefly, after equilibration of the skin membranes for about 15 min, 40 μl of tritiated water (1 kBq) were applied to the skin surface for 20 min. The receptor fluid flow was regulated to deliver about 0.2 mL/h. The unabsorbed fluid was then blotted with a cotton-tipped applicator and 40 pL PBS was applied to the skin surface. Effluent from the flow cell was collected for an additional 60 min. Skin was regarded as being undamaged if not more than 2% of the applied radioactivity were recovered from the receptor fluid.

B. Protocol

Two different formulations were tested: Formulation 1 (Example 1) and, as reference, Zovirax was chosen.

For each formulation, 3 replicates were set up for each sampling time, due to high inter-individual variability. At all sampling times, skin, receptor fluid and remaining test and reference product were recovered for analytical analysis.

The number of applications of the reference and test formulations, on 7 mg/skin disc (corresponding to 9 mg/cm²), was 5 times in 24 h (times of application 0 h, 4 h, 8 h, 12 h, 16 h), following the recommended dosage of the manufacturer's reference instructions. The test/reference item was not removed at any time but added to the previously applied formulation.

Collection of the receptor fluid started at time point t 0 h. The receptor fluid flow was regulated to deliver about 0.2 mL/h.

At time points 2 h, 6 h, 10 h and 24 h the corresponding samples of skin, receptor fluid, and skin rinses were collected for their subsequent LC-MS analysis.

At the end of the exposure period, the residual remaining test and reference product was wiped from the donor side of the diffusion cell as well as from the skin surface with a cotton bud. Additionally various rinse steps with the PBS receptor fluid were performed to remove the remaining test/reference item. The cotton buds and the rinsing liquid were stored at −15° C. for further analysis of the remaining test and reference product.

The skin discs and the collected receptor fluid were stored at 5.15° C. for further analysis.

C. Data Analysis

All samples were stored frozen until the analysis was performed.

At the moment of the analysis, the skin samples, and the remaining test and reference product samples were treated to extract all the acyclovir. This was performed with a skin homogenization using a FastPrep24 system (MP Biomedicals) followed by heat extraction (60° C., 30 min) and protein precipitation, using acetonitrile.

After the precipitation of acyclovir in all the samples to be analysed, a LC-MS/MS detection procedure was followed. Briefly, a liquid chromatographic system (Agilent 1200 series) with mass detector (AB Sciex, API 4000™) containing Analyst version 1.4.2 data system were used.

For the chromatographic separation of compounds a HPLC column (Luna Hilie (3 tim, 100×2.0 mm, Phenomenex) with isocratic gradient conditions with acetonitrile and 50 mM ammonium formate as mobile phase were used.

The specific conditions were:

| | |
|---|---|
| Injection volume: | 10 [AL |
| Sample storage | 4° C. |
| Oven temperature: | 30° C. |
| Flow rate: | 400 [1 L/min |
| Solvent: | 50 mM ammonium formate:acetonitrile, 10/90 (v:v), isocratic |
| Run time: | 5 min |
| Retention time: | ACV: approx. 3 min |
| | GCV: approx. 3.6 min |
| Detection: | Mass transfer ACV: 226.14/152.0 amu |
| | GCV: 256.3/152.0 amu |

From the data obtained, the percutaneous absorption profile was generated.

D. Results

In FIG. 1, wherein the amount of acyclovir is determined in skin, it can be observed that there is a substantial accumulative effect when the composition of the invention is administered. In fact, it is shown that at 10 and 24 h the amount of acyclovir available on the skin surface is significantly higher when compared to the amount obtained when the reference formulation is applied.

These data supports the fact that the combination of the invention, provides a matrix within which the active ingredient is highly bioavailable.

In addition, such "accumulative" effect observed with the formulation of the invention is an indicia of its strong bioadhesive profile. In order to get such a behavior, the combination of the invention adheres to the body tissue where it is applied, forming a thin film (which is the responsible of the high bioadhesivity observed with the combination of the invention). Due to this strong bioadhesion and the physico-chemical environment properties of the gel matrix (determined by the excipients, percentages, and ratios forming the combination of the invention), the active ingredient diffuses from the gel matrix and penetrates the skin.

The above is further supported by the data of Table 3, wherein it is indicated the amount of acyclovir on skin after several washes with receptor fluid:

TABLE 3

| Sample | Amount of Acyclovir (%) | | | | | | | |
|---|---|---|---|---|---|---|---|---|
| | t = 2 | | t = 6 | | t = 10 | | t = 24 | |
| | mean | SD | mean | SD | mean | SD | mean | SD |
| Formulation 1 | 3.14 | 2.54 | 1.47 | 0.53 | 6.11 | 3.83 | 9.69 | 4.87 |
| Zovirax | 0.88 | 0.00 | 0.78 | 0.13 | 1.10 | 0.83 | 0.46 | 0.14 |

As one can see, the amount of acyclovir detected in skin is at least 2-fold when Formulation 1 is applied to the skin, in comparison to the amount of the drug when the reference composition is applied.

Figure 2:
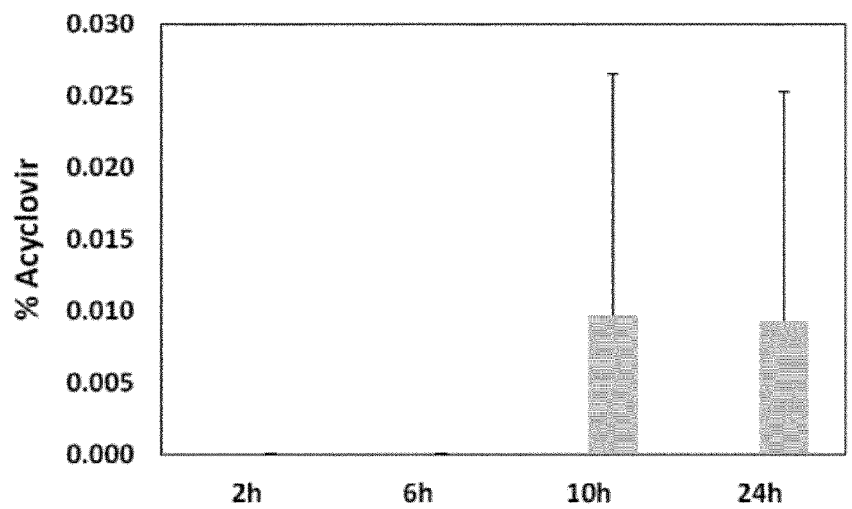
FIG. 2 shows the total amount of acyclovir (%) in the receptor fluid after 5 applications of Formulation 1 (black bar) or of the reference composition (grey bar) at times 2, 6, 10 h, and 24 h. Y-axis: mg acyclovir; X-axis: time (expressed in hours) at which the samples are taken.

In addition, in FIG. 2 it is shown that no acyclovir is detected in the receptor fluids collected when the formulation applied is the one of Example 1, on the contrary to the results obtained with the reference formulation. This is indicative that the matrix provided by the combination of the information confers an appropriate environment to the drug included within, in such a way that it is delivered in a sustained way, penetrates the skin but do not get the systemic circulation.

E. Conclusions

This means that the combination of the invention provides a matrix which: (a) do not negatively affect to the bioavailability of the drug but on the contrary, guarantees a substantial drug bioavailability, (b) said drug remains in the skin during a longer period of time (which explains such as accumulative effect), (c) shows a better bioadhesive profile than the reference composition, guaranteeing, even under adverse conditions (such as skin rinses), an amount of the active ingredient of at least the double of the one available with with the reference composition, and (d) the drug do not get the systemic circulation.

From the results obtained, therefore, it can be concluded that the combination of the present invention can be used to formulate pharmaceutical or veterinary compositions using lower amounts of the active ingredient or reducing the dosage/number of applications to obtain the desired therapeutic effect.

Summarizing, the composition of the invention provides important additional commercial advantages as the generation of a hydrophilic bioadhesive film which acts as a reservoir or matrix release ensuring the permanence of the active substance for longer when compared to conventional treatments. Its bioadhesive properties together with its aesthetic properties (transparency) facilitate patient compliance (reduced average duration of the treatment).

Although these assays have been performed with Formulation 1, the skilled person in the art will recognize that the advantages pointed out in this example as well as through all the specification, are due to the combination of excipients, in the specified ratios and weight percentages.

Example 4

Toxicology Assays for Formulation 1

Acyclovir is a widely known substance whose safety profile is well established. However, to check the safety profile of the combination of the invention, a battery of safety studies and regulatory tolerance were performed with Formulation 1 (in this section also referred as "test product"), among which a dermal tolerance study in rabbit at single dose, a dermal tolerance study in rabbit at repeated doses, and an ocular tolerance study in rabbits at single dose are included below.

As a reference, it was used the vehicle of Formulation 1, that is: polycarbophil (Noveon AA-1): 3 g; PVP 30: 6 g; Menthol crystal: 0.10 g; Trometamol: 3 g; Glycerine: 2 g; Propyleneglycol: 30 g; and deionized water: 55.90 g. All the components were mixed as described under Example 1.

As it is concluded, Formulation 1 has excellent skin tolerability under clinical use conditions with at least the same margin of safety and efficacy as its reference product.

Example 4.1

Ocular Tolerance Study in Rabbits at Single Dose: Acute Ocular Irritation/Corrosion A) Objective The purpose of this study was to assess the ocular tolerance (irritation/corrosion test) of Formulation 1, after a single dose application in the conjunctival sac of rabbits.

In this study was essential to proceed to a complete assessment of the symptoms (intensity, time of onset, reversibility) produced by the product, in order to obtain the degree of irritation or corrosion. In the study the untreated eye was used as control.

B) Test Conditions

Initial Test (Irritation/Corrosion):

New Zealand rabbits received a single application of 0.1 mL of the test product in the conjunctival sac of the right eye. The left eye was untreated and served as control.

After 72 hours of administration, and in the absence of corrosion, we proceeded to the realization of the following confirmatory test.

Confirmatory Test (Irritation):

In the absence of severe irritation, two New Zealand rabbits received simultaneously, a single application of 0.1 mL of the test product in the conjunctival sac of the right eye. The left eye of both rabbits was not treated and served as control.

Since corrosive or irritant effects were not detected for 72 hours, it was not necessary to evaluate the reversibility and the study was terminated. Thus, for each of the 3 animals, the observation period was of 3 days (72 hours).

C) Procedure

Animals were identified and distributed in individual cages. After the acclimation period began the initial test and, for this, 24 hours prior to administration, we proceeded to examine the eyes of the first animal, using a magnifying glass and a flashlight. The animal identified as 1, received a single application dose of 0.1 mL of the test product in the conjunctival sac of the right eye. The product was applied by gently pulling the lower lid to the outside of the eyeball. Once applied, the eyelids were held together for about one second, in order to prevent material loss. The left eye was untreated and served as control. In the absence of signs of corrosion or severe irritation, we performed the confirmatory test and, for this, we proceeded simultaneously with the other two animals of the study (labeled 2 and 3) in the same manner as described above.

No animal showed ocular irritation, ocular defects or alterations of the cornea prior to administration, so all animals could be used. The animals were submitted to study that included: clinical examination and evaluation of the ocular irritation/corrosion, as detailed below.

D) Clinical Examination

Viability/mortality: daily, for 3 days after administration.

Weight of the animal: to the arrival of the animals, at the beginning and before slaughter, as PNT-BT-502.

General symptoms: before and after the administration, and daily for 3 days after.

E) Eye Corrosion Evaluation

Ocular corrosion was evaluated as part of the initial test, immediately after application of the product and 1, 24, 48 and 72 hours later. It was assessed, in terms of presence-absence, lesions considered irreversible as: perforation or significant corneal ulceration, ulceration or conjunctival necrosis, necrosis of the nictitating membrane, ocular hemorrhage, grade 4 corneal opacity that persists for 48 hours and no reaction of the iris to light of grade 2 that persists for 72 hours.

At the time of the evaluation one hour after application, there were no remnants of the test product, so it was not necessary to wash with saline.

F) Eye Irritation Evaluation

The ocular irritation was assessed for the 3 animals of the study (initial and confirmatory assay); 1, 24, 48 and 72 hours after product application. In the absence of disturbances, it was not necessary to study the reversibility and the study ended after 72 hours of the treatment.

It was observed the degree and nature of irritation, as well as any histopathological lesion. The evaluation of the ocular lesions was performed with the animal immobilized in special traps. The reaction was evaluated ocular (numerical values between 0 and 4) according to Table 4:

TABLE 4

| OCULAR IRRITATION TEST (OECD TG-405) | |
|---|---|
| Cornea | |
| Absence of ulceration/opacity | 0 |
| diffuse opacity (details of iris clearly visible) | 1 |
| translucent area (details of iris slightly obscured) | 2 |
| necrotic area (no visible iris details) | 3 |
| Cloudy cornea | 4 |
| Maximum value | 4 |
| Iris | |
| Normal | 0 |
| Congestion, swelling, iris reactive to light | 1 |
| Hemorrhage, gross destruction, lack of reactivity to light | 2 |
| Maximum Value | 2 |
| Conjunctiva | |
| Average | 0 |
| Blood Blisters | 1 |
| diffuse crimson | 2 |
| Dark red fuzzy | 3 |
| Maximum value | 3 |
| Edema | |
| Normal | 0 |
| Swelling light | 1 |
| Swelling obvious | 2 |
| Swelling with eyelids half closed | 3 |
| Swelling with eyelids practically dosed | 4 |
| Maximum value | 4 |

Once finalized the pilot phase, animals were sacrificed by lethal injection, previous sedation. Both eyes of all animals were extracted, for anatomopathology analysis. The samples were fixed in 10% formaldehyde, and processed, carved and sent to the CIMA Morphology Service for their inclusion, cutting and staining (Hematoxylin-Eosin) and for performing histological preparations. The anatomopathological examination of these preparations was made by the Anatomopathological Diagnosis Service for Laboratory Animals (DAPAL) of the University of Zaragoza.

H) Results and Discussion

H.1. Viability/mortality and general symptoms: no lethality was registered in any of the animals which have been administered the test product. The experimental animals showed no alterations in overall condition.

H.2. Macroscopic assessment of ocular corrosion: the study of ocular corrosion made in the initial test did not show the presence of irreversible damage, such as perforation or significant corneal ulceration, ulceration or conjunctival necrosis, necrosis of the nictitating membrane, ocular hemorrhage, grade 4 corneal opacity that persists for 48 hours and no reaction of the iris to light of grade 2 that persists for 72 hours.

H.3. Macroscopic assessment of ocular irritation: as reflected in Table 5, after application of the test product, no edema or alterations were observed in the conjunctiva, iris or cornea.

TABLE 5

Assessment of ocular irritation. Individualized data.

| Animal identification | Assessment time | CORNEA | IRIS | CONJUNCTIVA | EDEMA |
|---|---|---|---|---|---|
| | 24 h | 0 | 0 | 0 | 0 |
| | 48 h | 0 | 0 | 0 | 0 |
| | 72 h | 0 | 0 | 0 | 0 |
| | 24 h | 0 | 0 | 0 | 0 |
| | 48 h | 0 | 0 | 0 | 0 |
| | 72 h | 0 | 0 | 0 | 0 |
| | 24 h | 0 | 0 | 0 | 0 |
| | 48 h | 0 | 0 | 0 | 0 |
| | 72 h | 0 | 0 | 0 | 0 |

TABLE 6

Alterations average in the cornea, iris, conjunctiva and edema. Individualized data.

| Animal identification | CORNEA AVERAGE | IRIS AVERAGE | CONJUNCTIVA AVERAGE | EDEMA AVERAGE |
|---|---|---|---|---|
| 1 | 0.0 | 0.0 | 0.0 | 0.0 |
| 2 | 0.0 | 0.0 | 0.0 | 0.0 |
| 3 | 0.0 | 0.0 | 0.0 | 0.0 |

It was determined that it was not irritant.

H.4. Microscopic findings: no morphological differences were observed between treated and control samples.

I) Conclusion

Formulation 1 was classified as not irritant.

The histological examination of the eyeballs did not establish morphological differences between treated and control samples.

Example 4.2

Dermal Tolerance Study in Rabbit at Repeated

A) Objective:

to assess the local tolerance of the test product in rabbits, after dermal repeated dose application of 1 mL/120 cm$^2$ (8.3 µL/cm$^2$), 4 times daily, up to a maximum of 10 days, with tolerance evaluation on days 1, 5 and 10. Furthermore, in order to evaluate the influence of the formulation vehicle on the tolerance data obtained, the study included the inclusion of a group of animals, in parallel to the treated group, which received the vehicle of the test product.

Finally, in order to assess the reversibility of the skin lesions that may occur after administration of the test product or its vehicle for 10 days, we included two groups of animals (reversal treated group and reversal vehicle group) in which, if it had been considered necessary, the observation period could be extended to 7 days after the last administration.

B) Test Conditions

Distribution

24 New Zealand male rabbits, in 2 groups (n=12) and—treated and vehicle—. Each group was divided into 4 subgroups (n=3)—a, b, c and reversal—.

Posology 4 daily dermal applications (range of 2.5 hours±15 minutes) of the test product of 1 mL/120 cm$^2$ (8.3 µL/cm$^2$). Applications were made in a shaved area of 120 cm$^2$ (about 10% of the body tissue). The number of applications depended on the subgroups and, for each animal, the starting day of treatment was considered the day 0:

Subgroup a: administration only one day (Day 0).
Subgroup b: daily administration for 5 days (Days 0-4, inclusive).
Subgroup c: daily administration for 10 days (Days 0-9, inclusive).
Subgroup reversal: daily administration for 10 days (Days 0-9, inclusive).

Observation Period:

treated and vehicle groups (subgroups a, b and c): Up to 16 hours after the last administration.
treated and vehicle groups (subgroups reversal): Up to 72 hours after the last administration.

C) Procedure

Animals were identified and distributed into two groups: treatment group and vehicle group, consisting of 12 animals. In turn, each group was divided into 4 subgroups—a, b, c and reversion—formed by 3 animals each. The animal housing was individualized.

The distribution of animals, administration schedule and observation, is reflected in Table 7:

TABLE 7

| Group/Subgroup | Administration time (days) | Administration product | Animal identification | Observation period (days) |
|---|---|---|---|---|
| Treated. Subgroup a | 1 | Test product (8.3 µL/cm2) | Green 1 to 3 | 1 |
| Treated. Subgroup b | 5 | Test product (8.3 µL/cm2) | Green 4 to 6 | 5 |
| Treated. Subgroup c | 10 | Test product (8.3 µL/cm2) | Green 7 to 9 | 10 |
| Treated. Subgroup reversal | 10 | Test product (8.3 µL/cm2) | Green 10 to 12 | 13 (10 + 3) |
| Vehicle. Subgroup a | 1 | Test product vehicle (8.3 µL/cm2) | Black 1 to 3 | 1 |
| Vehicle. Subgroup b | 5 | Test product vehicle (8.3 µL/cm2) | Black 4 to 6 | 5 |
| Vehicle. Subgroup c | 10 | Test product vehicle (8.3 µL/cm2) | Black 7 to 9 | 10 |
| Vehicle. Subgroup reversal | 10 | Test product vehicle (8.3 µL/cm2) | Black 10 to 12 | 13 (10 + 3) |

Animals were shaved, and an area of 12 cm×10 cm (120 cm$^2$) was marked with indelible ink in the back of the animal (approximately 10% of body tissue), and care was taken in order to preserve the area clearly identifiable throughout the study, shaving and highlighting the area whenever necessary. In that area, the animals received daily, 4 administrations of 1 mL of the test product or its vehicle (8.3 µL/cm$^2$ of surface area), with an interval of 2.5 hours±15 minutes, for 1, 5 or 10 days according to the subgroup.

The application was made dermally and, for that, a syringe was charged with 1 mL of the test product (or test product vehicle) was deposited in the center of the marked area on the back of the animal (application area) and, with the hand, the product to be applied was distributed in all the delimited area. The animal did not return to the cage until it was observed the formation of a non-sticky adhesive film. In no case the administration area was washed, so even when during the following administration remains of the adhesive film were observed, the new application was made above it.

The animals of all groups/subgroups were submitted to a study that included: clinical examination and evaluation of the local tolerance, as detailed below.

D) Clinical Examination

Viability/mortality: daily

General symptoms: the animal behavior was monitored daily during the administration period. The study included the evaluation of the general conditions, activity, body position, color of the skin, eyes, mucous membranes and the presence/absence of seizures, tremors, diarrhea and pilo-erection. Weight of the animal: at the arrival of the animals, at the beginning, and before slaughtering.

E) Local Tolerance Evaluation (Macroscopic Evaluation):

the nature and magnitude of the observed reaction were assessed macroscopically. It was evaluated the presence of erythema, edema, desquamation. The observation days were day 1 for subgroups a, b, c and reversal; day 5 for subgroups b, c and reversal; and day 10 for the group c and reversal. In order to study the reversibility of the alterations observed after 10 days of treatment, the evaluation of the reversal subgroup at the times 24, 48 and 72 hours after the last administration (days 10, 11 and 12) was performed.

Animals were sacrificed by lethal injection, previous sedation.

Then, skin samples were obtained, carved, and sent to the CIMA Morphology Service for their inclusion, cutting and staining (Hematoxylin-Eosin). The anatomopathological examination was made by the Anatomopathological Diagnosis Service for Laboratory Animals (DAPAL) of the University of Zaragoza.

F) Results and Discussion

F.1. Viability/mortality and general symptoms: no mortality in any of the animals, administered with the test product or its vehicle, was registered. Animals showed no alterations in their general condition, during the treatment days.

TABLE 8

| Viability/mortality. Individualized data of the treated groups | | | | | | | | | | | | | |
|---|---|---|---|---|---|---|---|---|---|---|---|---|---|
| Animal | Days of the study | | | | | | | | | | | | |
| identification | 0 | 1 | 2 | 3 | 4 | 5 | 6 | 7 | 8 | 9 | 10 | 11 | 12 |
| 1 Treated a | V | * | | | | | | | | | | | |
| 2 Treated a | V | * | | | | | | | | | | | |
| 3 Treated a | V | * | | | | | | | | | | | |
| 4 Treated b | V | V | V | V | V | * | | | | | | | |

TABLE 8-continued

Viability/mortality. Individualized data of the treated groups

| Animal identification | Days of the study | | | | | | | | | | | | |
|---|---|---|---|---|---|---|---|---|---|---|---|---|---|
| | 0 | 1 | 2 | 3 | 4 | 5 | 6 | 7 | 8 | 9 | 10 | 11 | 12 |
| 5 Treated b | V | V | V | V | V | * | | | | | | | |
| 6 Treated b | V | V | V | V | V | * | | | | | | | |
| 7 Treated c | V | V | V | V | V | V | V | V | V | V | V | * | |
| 8 Treated c | V | V | V | V | V | V | V | V | V | V | V | * | |
| 9 Treated c | V | V | V | V | V | V | V | V | V | V | V | * | |
| 10 Treated reversal | V | V | V | V | V | V | V | V | V | V | V | V | * |
| 11 Treated reversal | V | V | V | V | V | V | V | V | V | V | V | V | * |
| 12 Treated reversal | V | V | V | V | V | V | V | V | V | V | V | V | * |

V: living animal
*programmed sacrifice

F.2. Macroscopic assessment: the administration of the test product at 4 applications/day during 1, 5 and 10 days evaluated in the subgroups treated a, treated b, treated c and treated reversal, did not produce signs of skin disorders in any of the treated animals (see Table 9).

Regarding the group of animals that received the vehicle, at day 5 (after 20 applications) it was observed the presence of very slight erythema (Grade 1) in two animals (those identified as 7 and 12). In the case of the animal 12, erythema was accompanied by desquamation of moderate intensity. The severity of erythema and desquamation, decreased until macroscopic evaluation performed on day 10 (after 40 applications). Evaluations in the animal 12 of the subgroup vehicle reversal, at 24, 48 and 72 hours after treatment, confirmed the resolution of erythema, while the desquamation remained with very low intensity, barely noticeable.

G) Conclusion

The dermal application of the test product in amount of 1 mL/120 cm$^2$ at 4 applications daily for 10 days, was non-irritant and completely safe.

Example 4.3

Dermal Tolerance Study in Rabbits at Single Dose: Acute Dermal Irritation/Corrosion A) Objective:

the purpose of this study was to evaluate the skin dermal tolerance (irritation/corrosion) of the test product after a single application dose on intact skin, in rabbits.

In order to evaluate the influence of the formulation vehicle in the observed effects, the study regarded its application in an independent separate area (considered as vehicle control area). Finally, in each animal, a not treated area served as negative control area.

B) Test Conditions

Initial Test (Irritation/Corrosion):

A New Zealand rabbit received a single 0.5 mL dose of both test product (treated area) and its vehicle (vehicle control area) applied dermally in the dorsal area of the animal, on a body tissue of approximately 6 cm2 for each administration area. The exposure period was 4 hours. In the absence of signs of corrosion within 72 hours, we proceeded to the realization of the following test (confirmatory test).

Confirmatory Test (Irritation Test):

Two New Zealand rabbits received a single dose of 0.5 mL of the test product (treated area) and its vehicle (vehicle control area) applied dermally in the dorsal area of the animal, on a body tissue of approximately 6 cm$^2$ for each application. The exposure period was of 4 hours. Observation period (considered as day 0 the day of the product

TABLE 9

Evaluation of the treated group dermal tolerance. Individualized data at days 1, 5 and 10

| Animal identification | Day 1 | | | Day 5 | | | Day 10 | | |
|---|---|---|---|---|---|---|---|---|---|
| | erythema | edema | desqua | erythema | edema | desqua | erythema | edema | desqua |
| 1 Treated a | 0 | 0 | 0 | | | | | | |
| 2 Treated a | 0 | 0 | 0 | | | | | | |
| 3 Treated a | 0 | 0 | 0 | | | | | | |
| 4 Treated b | 0 | 0 | 0 | 0 | 0 | 0 | | | |
| 5 Treated b | 0 | 0 | 0 | 0 | 0 | 0 | | | |
| 6 Treated b | 0 | 0 | 0 | 0 | 0 | 0 | | | |
| 7 Treated c | 0 | 0 | 0 | 0 | 0 | 0 | 0 | 0 | 0 |
| 8 Treated c | 0 | 0 | 0 | 0 | 0 | 0 | 0 | 0 | 0 |
| 9 Treated c | 0 | 0 | 0 | 0 | 0 | 0 | 0 | 0 | 0 |
| 10 Treated reversal | 0 | 0 | 0 | 0 | 0 | 0 | 0 | 0 | 0 |
| 11 Treated reversal | 0 | 0 | 0 | 0 | 0 | 0 | 0 | 0 | 0 |
| 12 Treated reversal | 0 | 0 | 0 | 0 | 0 | 0 | 0 | 0 | 0 |

Qualitative assesment of erythema, edema and desquamation expressed as:

Erythema:
Absence . . . 0
Very light (barely perceptible) . . . 1
Well-defined . . . 2
Moderate-severe . . . 3
Severe erythema (beet red) To crusting . . . 4

Edema:
Absence . . . 0
Very light (barely perceptible) . . . 1
Well-defined . . . 2
Moderate-Severe (approx 1 mm) . . . 3
Severe edema (more than 1 mm outside the area of exposure) . . . 4

Desquamation:
Absence . . . 0
Mild (barely perceptible) . . . 1
Moderate . . . 2
Severe (flakes emerge from skin) . . . 3

Note:
In any evaluation there was any other sign, such as ulcers, bleeding, crusting or other.

application): Since were not detected corrosive or irritant effects for 72 hours, it was not necessary to evaluate the reversibility and the study was terminated. Thus, for each of the 3 animals, the observation period was of 3 days (72 hours).

C) Procedure

Animals were identified and distributed in individual cages.

After the acclimation period began the initial test and, for this, approximately 24 hours before application the back of the first animal carefully shaved.

For the dermal administration a syringe was charged with 0.5 mL of test product, which was deposited in the center of the treated marked area on the back of the animal and, by hand, the product was spread throughout the defined area. Then we proceeded equally with the vehicle. 90 minutes after administration, gauze was placed in each administration area. Finally, an elastic bandage was placed around the gauze, which was clamped with tape. The dressing pad was removed 4 hours after application. Both areas were assessed, immediately after removal of the bandage and 1, 24, 48 and 72 hours later.

Since no corrosive effects were detected after 72 hours, we proceeded to the confirmatory test. For this, we proceeded similarly with the other two animals of this study. The three animals were submitted to a study that included: clinical examination and assessment of skin irritation, as detailed below.

D) Clinical Examination

Viability/mortality: daily, for 3 days after administration.

Weight of the animal: to the arrival of the animals, at the beginning and before slaughter.

General symptoms: before and after the administration, and daily for 3 days after.

E) Skin Corrosion Evaluation

The skin corrosion was evaluated as part of the initial test, after removal of the bandage and 1, 24, 48 and 72 hours later. The reaction was evaluated in terms of presence-absence for ulcers, bleeding and crusting with hemorrhagic component.

F) Skin Irritation Evaluation

Skin irritation was evaluated for the 3 animals in the study (initial and confirmatory test) 1, 24, 48 and 72 hours after removal of the bandage. No changes were observed so it was no necessary to extend the study period. It was observed the degree and the nature of irritation, as well as possible histopathological lesion. Skin reactions were evaluated (numerical values between 0 and 4) according to the following table (dermal evaluation scale adopted from the OECD guide 404). It was analysed the presence of other local skin reactions, and well as any systemic effect.

| Skin irritation test | |
|---|---|
| Erythema | |
| Absence of erythema | 0 |
| Very slight erythema (barely perceptible) | 1 |
| well defined erythema | 2 |
| moderate to severe erythema | 3 |
| Severe erythema (beet red) to crusting | 4 |
| Maximum value | 4 |
| Edema | |
| Absence of edema | 0 |
| very slight edema (barely perceptible) | 1 |
| Slight edema | 2 |
| moderate edema (extended approximately 1 mm) | 3 |
| Severe edema (greater than 1 mm, outside the exhibition area) | 4 |
| Maximum value | 4 |

G) Pathology

Once finalized the experimental phase, animals were sacrificed by lethal injection, previous sedation.

Skin samples were taken from the treated areas (with the test product and with its vehicle) and from the negative control area (untreated area) of all animals, for anatomopathological study. Samples were fixed in 4% formaldehyde and processed, carved, and sent to the CIMA Morphology Service for their inclusion, cutting and staining (Hematoxylin-Eosin) and for performing histological preparations. The anatomopathological examination of these preparations was made by the Anatomopathological Diagnosis Service for Laboratory Animals (DAPAL) of the University of Zaragoza.

H) Results and Discussion

H.1. Viability/mortality and general symptoms: no lethality was registered in any of the animals which have been administered the test product. The experimental animals showed no alterations in overall condition.

H.2. Macroscopic assessment of skin corrosion: as reflected in Tables 10 and 11, the skin corrosion study performed in the initial test did not show the presence of ulcers, bleeding or crusting in areas where the test product, or its vehicle, was applied.

TABLE 10

Skin corrosion evaluation with the test product. Individualized data

| Animal identification | Assessment time* | ULCERS | BLEEDING | CRUSTING |
|---|---|---|---|---|
| 1 | 0 h (after removal of the dressing) | — | — | — |
| | 1 h | — | — | — |
| | 24 h | — | — | — |
| | 48 h | — | — | — |
| | 72 h | — | — | — |

—: Absence;
*in hours, since the bandage removal

TABLE 11

Skin corrosion evaluation with vehicle. Individualized data

| Animal identification | Assessment time* | ULCERS | BLEEDING | CRUSTING |
|---|---|---|---|---|
| 1 | 0 h (after removal of the dressing) | — | — | — |
| | 1 h | — | — | — |
| | 24 h | — | — | — |
| | 48 h | — | — | — |
| | 72 h | — | — | — |

—: Absence;
*in hours, since the bandage removal

H.3. Macroscopic assessment of skin irritation: as reflected in Tables 12 and 13, the skin irritation study showed no presence of erythema, edema or any other reactions in the areas where the test product or its vehicle were applied.

TABLE 12

Skin irritation evaluation with the test product. Individualized data

| Animal identification | Assessment time | ERYTHEMA | EDEMA |
|---|---|---|---|
| | 24 h | 0 | 0 |
| | 48 h | 0 | 0 |
| | 72 h | 0 | 0 |
| | 24 h | 0 | 0 |
| | 48 h | 0 | 0 |
| | 72 h | 0 | 0 |
| | 24 h | 0 | 0 |
| | 48 h | 0 | 0 |
| | 72 h | 0 | 0 |

TABLE 13

Skin irritation evaluation with the vehicle. Individualized data

| Animal identification | Assessment time | ERYTHEMA | EDEMA |
|---|---|---|---|
| | 24 h | 0 | 0 |
| | 48 h | 0 | 0 |
| | 72 h | 0 | 0 |
| | 24 h | 0 | 0 |
| | 48 h | 0 | 0 |
| | 72 h | 0 | 0 |
| | 24 h | 0 | 0 |
| | 48 h | 0 | 0 |
| | 72 h | 0 | 0 |

I) Conclusion

The Skin Irritation Index (IIC) calculated for the test product has a value of zero. It was observed the absence of erythema, edema or other reactions in the application areas. In accordance with above, it was concluded that the test product is classified as no irritant.

The histological examination of the areas that received the test product or vehicle showed no significant alterations. The findings described that, for both areas, and for one of the animals, very low intensity alterations with no clinical significance, considered as a reversible adaptation mechanism of the skin.

The invention claimed is:

1. A combination comprising:
polycarbophil in an amount from 1 to 5% by weight,
polyvinylpirrolidone in an amount from 4 to 8% by weight,
glycerine in an amount from 1 to 10% by weight, and
propyleneglycol in an amount from 20 to 40% by weight, wherein:
the weight ratio polyvinylpirrolidone:polycarbophil is between 1:1 and 4:1,
the weight ratio glycerine:polycarbophil is from 0.5:1 to 2:1, and
the weight ratio propyleneglycol:polycarbophil is from 8:1 to 20:1.

2. The combination according to claim 1, wherein the weight ratio polyvinylpirrolidone:polycarbophil is 2:1.

3. The combination according to claim 1, wherein the weight ratio between glycerine:polycarbophil is from 0.5:1 to 1:1.

4. The combination according to claim 1, wherein the weight ratio propyleneglycol:polycarbophil is 10:1.

5. The combination according to claim 1, which further comprises a pH regulating agent.

6. The combination according to claim 5, wherein the pH regulating agent is trometamol.

7. The combination according to claim 1 comprising:
polycarbophil: 3% by weight
polyvinylpirrolidone: 6% by weight,
glycerine: 2% by weight,
propyleneglycol: 30% by weight, and
trometamol: 3% by weight.

8. A pharmaceutical or veterinary composition comprising the combination as defined in claim 1, together with: (a) a therapeutically effective amount of an active ingredient or a pharmaceutically or veterinary acceptable salt thereof; and (b) other appropriate pharmaceutically or veterinary acceptable excipients and/or carriers.

9. The pharmaceutical or veterinary composition according to claim 8, which is in the form of a gel.

10. A process for preparing the pharmaceutical or veterinary composition as defined in claim 8, the process comprising the following steps:
(a) mixing the active ingredient or pharmaceutically or veterinary salt thereof with propyleneglycol under agitation;
(b) adding the polyvinylpirrolidone;
(c) adding the glycerine;
(d) adding the polycarbophil; and
(e) adding the other appropriate pharmaceutically or veterinary acceptable excipients and/or carriers.

11. A kit comprising a combination as defined in claim 1.

12. A method of forming a gel comprising using the combination according to claim 1, as a gel-forming agent.

13. A method of use of the combination according to claim 1, as a film-forming agent comprising depositing the combination on a body tissue, absorbing the moisture from the tissue, and forming a film over the surface of the body tissue.

14. A pharmaceutical or veterinary composition comprising the combination as defined in claim 7, together with: (a) a therapeutically effective amount of an active ingredient or a pharmaceutically or veterinary acceptable salt thereof; and (b) other appropriate pharmaceutically or veterinary acceptable excipients and/or carriers.

15. The pharmaceutical or veterinary composition according to claim 14, which is in the form of a gel.

16. A process for preparing the pharmaceutical or veterinary composition as defined in claim 14, the process comprising the following steps:
(a) mixing the active ingredient or pharmaceutically or veterinary salt thereof with propyleneglycol under agitation;
(b) adding the polyvinylpirrolidone;
(c) adding the glycerine;
(d) adding the polycarbophil; and
(e) adding the other appropriate pharmaceutically or veterinary acceptable excipients and/or carriers.

17. A kit comprising a pharmaceutical or veterinary composition as defined in claim 14, and a support.

18. A kit comprising a pharmaceutical or veterinary composition as defined in claim 16, and a support.

* * * * *